United States Patent [19]

Schaldach

[11] Patent Number: 5,318,592
[45] Date of Patent: Jun. 7, 1994

[54] CARDIAC THERAPY SYSTEM

[75] Inventor: Max Schaldach, Erlangen, Fed. Rep. of Germany

[73] Assignee: BIOTRONIK, Mess- und Therapiegeräte GmbH & Co., Ingenieurbüro Berlin, Berlin, Fed. Rep. of Germany

[21] Appl. No.: 943,249

[22] Filed: Sep. 14, 1992

[30] Foreign Application Priority Data

Sep. 12, 1991 [DE] Fed. Rep. of Germany ....... 4130595

[51] Int. Cl.$^5$ ............................................... A61N 1/36
[52] U.S. Cl. .......................................... 607/5; 600/17
[58] Field of Search .................... 128/419 PG, 419 D; 600/16, 17, 18

[56] References Cited

U.S. PATENT DOCUMENTS

| | | | |
|---|---|---|---|
| 4,719,921 | 1/1988 | Chirife | 128/419 PG |
| 4,733,667 | 3/1988 | Olive et al. | 128/419 PG |
| 4,804,358 | 2/1989 | Karcher et al. | 600/17 |
| 5,040,536 | 8/1991 | Riff | 600/17 |

Primary Examiner—William E. Kamm
Assistant Examiner—Scott M. Getzow
Attorney, Agent, or Firm—Spencer, Frank & Schneider

[57] ABSTRACT

A cardiac therapy system for use with a conventional cardiac pacemaker circuit is controlled by activity signals of the autonomous nervous system (ANS) in a patient's body which constitute a measure for the patient's cardiovascular output requirement. The system includes pickup circuitry for detecting at least the autonomous nervous system activity signals in the patient's body, a control circuit for generating control signals as a function of time and/or intensity of the autonomous nervous system signals picked up in the patient's body, a neurostimulator for changing vascular resistance by nerve stimulation of the patient in adaptation to the patient's intracardial output requirement, in response to control signals from the control circuit, an arrythmia suppressor for generating anti-arrhythmia stimulation pulses to the patient's heart which are controlled by control signals from the control circuit, and a pump assist for assisting the pumping of the patient's heart in response to control signals from the control circuit.

14 Claims, 3 Drawing Sheets

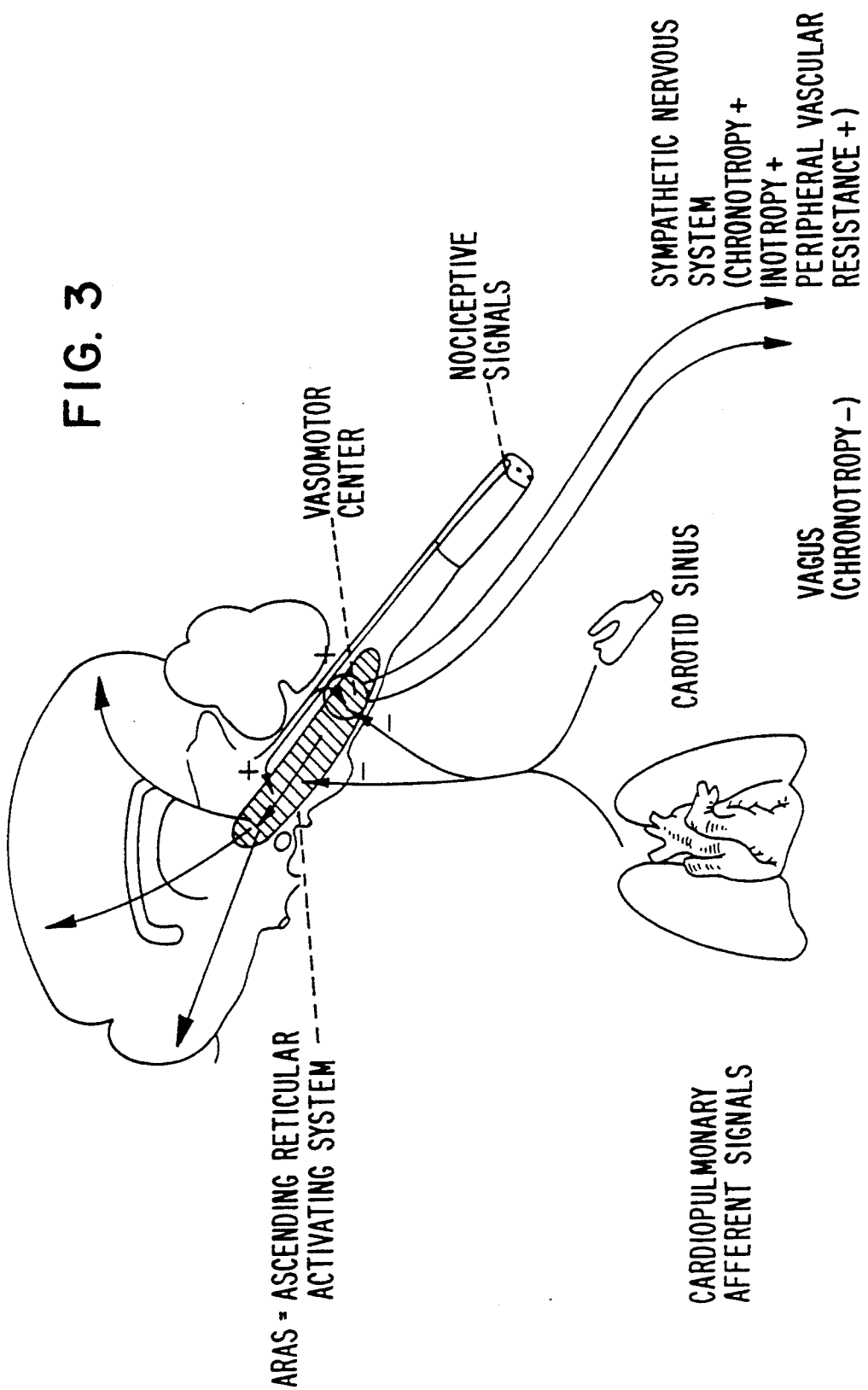

CARDIAC THERAPY SYSTEM

BACKGROUND OF THE INVENTION

1. Field of The Invention

The invention relates to a cardiac therapy system of the type including control by activity signals of the autonomous nervous system.

2. Background Information

In connection with cardiac pacemakers it is known to utilize values picked up from the patient's body and representing external stress or the stress on the body's organs to control cardiac stimulation. Additionally it is known to utilize those signals which are exclusively a measure for the cardiovascular heart output requirement and thus constitute information from the autonomous nervous system (ANS).

It has been found that a number of heart diseases cannot be treated solely by pacemaking stimulation pulses.

SUMMARY OF THE INVENTION

It is the object of the invention to broaden the range of treatments in a cardiac therapy system of the abovementioned type.

This is accomplished by a system which includes pickup circuitry for detecting at least the autonomous nervous system activity signals in that patient's body, a control circuit for generating control signals as a function of time and/or intensity of the autonomous nervous system signals picked up in the patient's body, the control signals for controlling at least one of a neurostimulator for changing vascular resistance by nerve stimulation of the patient in adaptation to the patient's intracardial output requirement, in response to control signals from the control circuit, an arrythmia suppressor for generating anti-arrhythmia stimulation pulses to the patient's heart which are controlled by control signals from the control circuit, and a pump assist for assisting the pumping of the patient's heart in response to control signals from the control circuit.

The invention is based on the realization that the information from the autonomous nervous system constitutes favorable input values not only for the generation of stimulation pulses but also for other therapy measures that affect the heart.

Particularly suitable for the generation of further signals that influence these therapy measures is the information from the autonomous nervous system because they are a direct measure of the internal cardiovascular heart output requirement and are not—as, for example, the pacemakers controlled by the patient's activity—derived from an external value by way of the stress, and are not linked to further stress or cardiovascular system values or are dependent upon them.

An analysis of the hemodynamics of the circulatory system indicates that the cardiovascular output can be sufficiently described in the form of a (negative feedback controlled system). The average arterial blood pressure is the controlled value and the cardiac output requirement is the controlling variable. Under physiological conditions, the short-term control of the average arterial blood pressure works well. All demands on the cardiovascular system are held in equilibrium and, therefore, furnish reliable perfusion of the tissue.

Most demands on the cardiovascular system influence the peripheral vascular resistance. The most relevant of these demands are: physical activity, skin temperature and the core temperature of the body, the acid level, the equilibrium and body posture. One of the demands influences the resistive, as well as the capacitive, characteristics of the periphery by changing the constriction of the arterioles or venules. The secondary effects are changes in vascular resistance, in blood pressure, in venal return flow and in cardiac output. For example, vascular resistance may change five fold during physical activity. To keep the blood pressure constant, venal return flow and cardiac output must be changed correspondingly in the opposite direction.

Cardiac output requirement is the controlling value. It is the product of the heart rate and stroke volume. Changes in cardiac output requirement are in an inverse relationship to the changes in vascular resistance with the result that the average arterial blood pressure is held essentially constant. Under physiological conditions, the adaptation of the cardiac output requirement to the changes in vascular resistance is effected by a (closed loop feedback) system including baroreceptors operating as pressure sensors in the aortal arc and in the carotid sinus. The output signals of these baroreceptors are fed to the medullar cardiovascular centers. These centers send output signals to the heart by way of the sympathetic or the parasympathetic nervous system.

The sympathetic nervous system regulates the sine frequency and the ventricular stroke volume. The parasympathetic nervous system, in contrast, influences primarily the heart rate. The combination of chronotropic and inotropic factors together leads to a control of the cardiac output. Other variables which influence the heart on the basis of the same external paths are, among others: pain, emotion and physiological stress.

In patients suffering from chronotropic insufficiency, the feedback mechanism, with which the heart rate is regulated by way of the sinoatrial node, is interrupted. As a consequence, these patients are able to react to stress only by a change in the stroke volume. However, the possible change in the stroke volume is very slight during physical activity.

In the past, stimulation therapy has offered various strategies for counteracting the influence of stress on the circulatory system.

The cardiac therapy system according to the invention, which provides a control by signals from the autonomous nervous system (ANS) that are a measure of the cardiovascular output requirement, is preferably employed in addition to a conventional cardiac pacemaker circuit.

Control signals are generated as a function of time and/or intensity of the ANS signals picked up in the patient's body and serve to change the vascular resistance by way of nerve stimulation so as to adapt it to the intracardial output requirement. In this way, vascular resistance and cardiac output can be adapted to one another. Many diseases of the circulatory system, such as disturbed blood circulation or vascular spasms, can be treated without chemotherapy. The stimulation treatment of the nerve conductors responsible for the respective vascular region adapts the vascular resistance to the momentary physiological output requirement so that it corresponds to the respective cardiovascular requirements. Because of it being possible to make short-term changes, the neurostimulation process disclosed here is superior to chemotherapy measures.

Moreover, anti-arrhythmia stimulation pulses can also be initiated and synchronized as a function of and in synchronism with ANS signals. These signals have an information content which enables them to act in such a way that they determine tachycardias and have a defibrillating effect since the signals from the autonomous nervous system, in a way, contain the "basic information" for the synchronism of the cardiac activity with the basic systems of the body that control it.

Correspondingly, the signals from the autonomous nervous system can also be used to activate and synchronize a pump assist system. For this purpose, advantage is taken of the fact that the missing required pump output, if the heart is insufficient in this respect, must be provided by the assist system in which case the required total output directly corresponds to the cardiovascular output requirement determined by the ANS.

The effect of the signals derived from the ANS signals can advantageously be logically linked, if required, with control signals picked up within the patient's body and constituting a measure for the external physical stress on the patient or the stress on body organs. For this purpose, the mentioned control signals are preferably correlated as a function of predetermined event patterns for each case, that is, as a function of the occurrence of the ANS signals within predetermined time windows, as a function of their frequency and/or intensity, and possibly of the further signals and/or external programming signals and/or control signals themselves that have been produced earlier in this manner.

A central, easily reproducible value furnished by the autonomous nervous system (ANS) and decisive for cardiovascular requirements is the regionally operative increase (ROI) of the intracardial impedance of the right ventricle. The interval in which the change is generally the greatest during isovolumetric contraction, and here again, the region exhibiting the greatest change during changes in stress on the patient, are selected with preference. Thus, the determined signal has useful characteristics which result in it being preferably suitable as a control signal for the parameters of the cardiac pacemaker that determine cardiac output.

The regionally operative increase is inversely proportional to myocardial contractility. The greater the contractility, the faster it must be possible to build up the pressure required to open the ventricular valves of the heart.

The ANS here provides autonomous nerve information that is substantially independent of further influential values and is representative of the cardiac output requirement. It exhibits an inotropic behavior indicative of cardiovascular requirements as a control signal for the re-establishment of chronotropic behavior and constitutes a value that is decisive for the modulation of contractility. It has been found that sufficient resolution ca be attained with a unipolar electrode that is disposed in the ventricle, in which case the cardiac pacemaker housing serves as the counter-electrode.

BRIEF DESCRIPTION OF THE DRAWINGS

Advantageous features of the invention are defined in the dependent claims and will be described in greater detail below together with a description of the preferred embodiment of the invention and with reference to the drawing figures, in which:

FIG. 3 is a schematic representation for neuruostimulation employing the invention.

DETAILED DESCRIPTION OF THE PREFERRED EMBODIMENT

Figure 1:
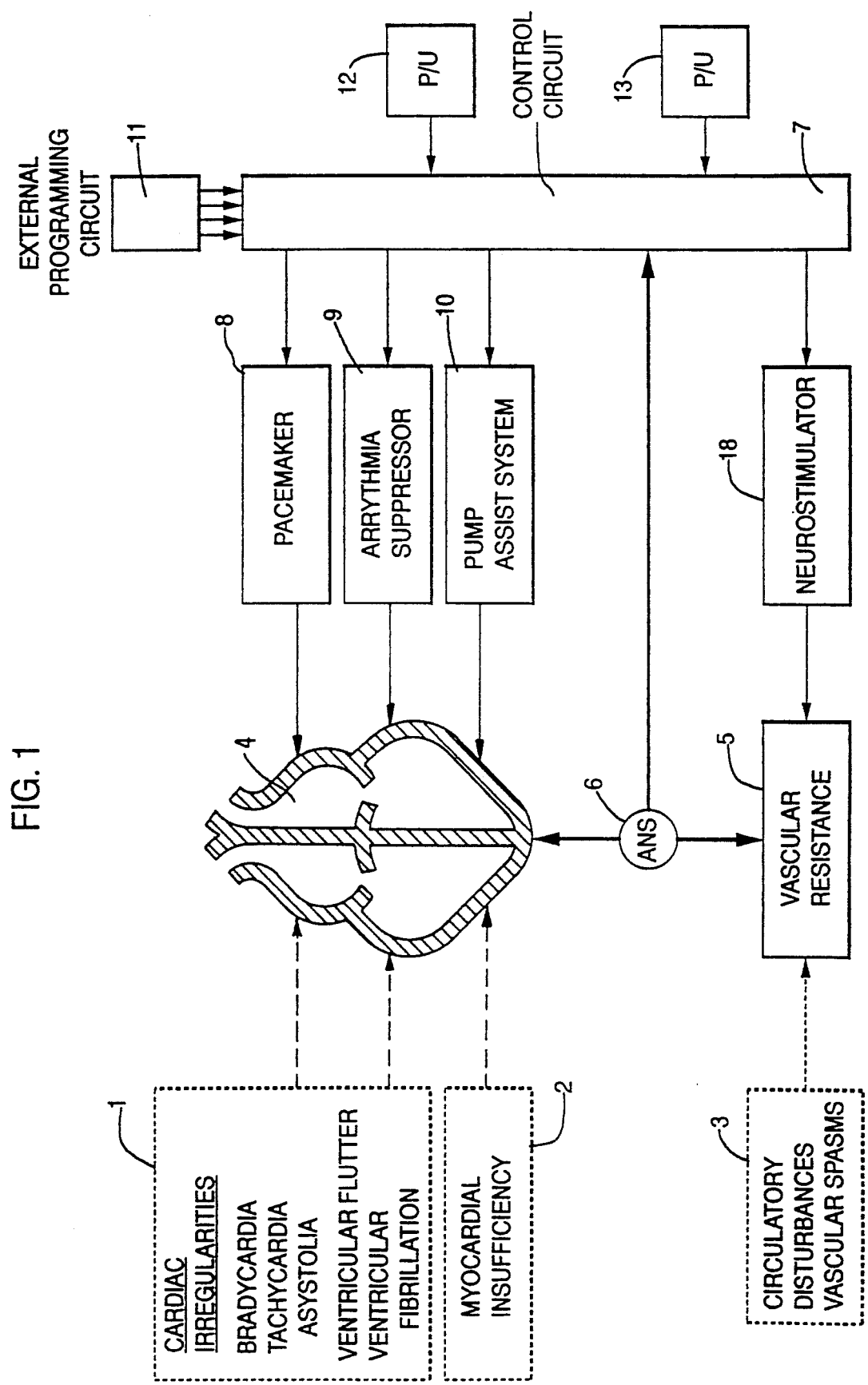
FIG. 1 is a block circuit diagram of an advantageous embodiment of the invention.

In the embodiment shown in FIG. 1, a number of cardiovascular diseases are listed in blocks 1 to 3 in the left-hand portion of the figure. These diseases have an influence on the cardiovascular system represented by the heart 3 and the vascular system 5 characterized by its resistance in the circuit.

In a block 6, a value ANS is derived as the circulation effective value of the autonomous nervous system. The value decisive for the cardiovascular output with respect to intensity and synchronism is further processed in a control circuit 7 shown in greater detail in FIG. 2.

A pacemaker 8 to stimulate the heart and an arrhythmia suppressor 9 for defibrillation and determination of tachycardias are connected to control circuit 7.

A pump assist system 10 replaces the heart muscle at least in part if there is an insufficiency in pumping activity.

By means of an external programming circuit 11, the internal signal linkages of control circuit 7 can be influenced, together with consideration, if necessary, of external signal pickups (P/U) 12 and 13 which compile signals picked up within the patient's body and outside of it, signals that are a measure for the external physical stress or the stress on individual organs of the patient, the latter again in dependence on external physical stress.

Figure 2:
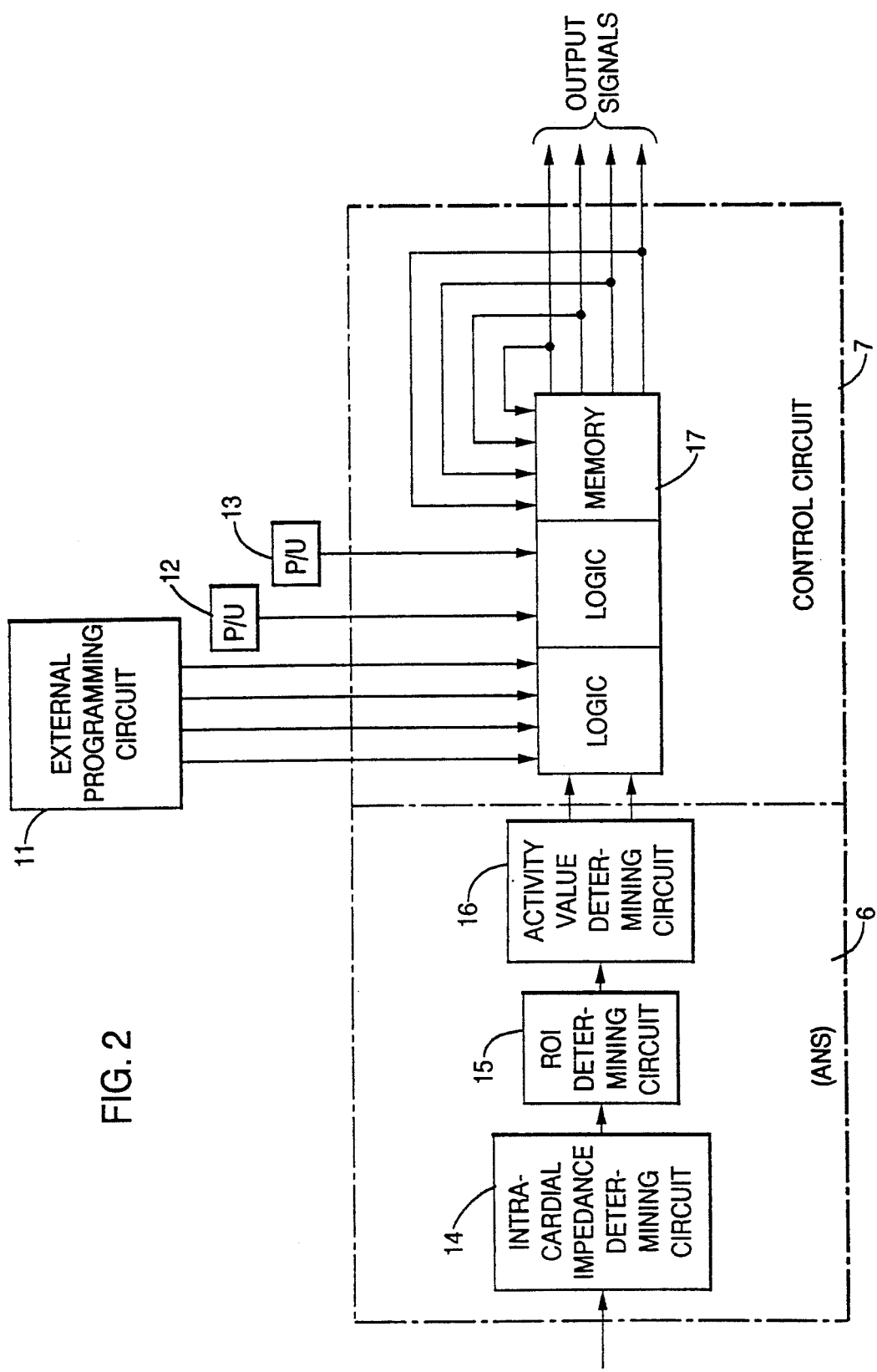
FIG. 2 is a detail view of part of the embodiment shown in FIG. 1.

The blocks 6 and 7 of the block circuit diagram of FIG. 1 shown in detail in FIG. 2, in the case of block 6, relate to the generation of a signal including the information from the autonomous nervous system signal.

In a first block 14, the intracardial impedance and in a block 15 the regionally operative increase (ROI) of the intracardial impedance in the region of the right ventricle are determined as the activity value of the autonomous nervous system. In a further subsequently connected block 16, the determination of the activity value is limited in each case to the region of maximum changes that are a function of the patient's activity. The two signal output lines of block 16 here each represent information of the activity value of the ANS signal relating to its intensity and time position during the cardiac time interval (synchronism).

In block 17, the input signals for the therapy system are logically linked to produce the required output signals to pacemaker 8, arrythmia suppressor 9, pump assist 10, and neurostimulator 18.

To accomplish this, control signals are generated as a function of time and/or intensity of the ANS signals picked up within the patient's body, by means of which the vascular resistance is changed by way of nerve stimulation in adaptation to the intracardial output requirement, anti-arrhythmia stimulation pulses are initiated and/or synchronized and a pump assist system is activated and/or synchronized. Block 17 here constitutes a memory for control sequences which can be called up as a function of the input signals. The input signals are here digitalized "addresses" for the memory so that—in the extreme case—for every input signal combination a corresponding output signal sequence is available for the respective blocks to be actuated.

The control signals are here initiated as a function of further signals picked up within the patient's body and constituting a measure for the external physical stress on the patient or the stress on body organs. These control signals are generated as a function of respectively predeterminable event patterns, that is, of the occurrence of the ANS signals within predetermined time windows, their frequency and/or intensity and, if required, of further signals and/or external programming signals and/or the control signals themselves that were generated earlier in this way.

FIG. 3 shows the principle of the influence of the circulation effective ANS activity due to nociceptive stimulation. The ANS activity picked u in the heart is used to influence the corresponding activity of other regions of the circulatory system so that here a correction can be made in the sense of the ANS activity picked up in the heart.

The invention is not limited in its embodiments to the above-described preferred embodiment. Rather, a number of variations are conceivable which take advantage of the described solution even for basically different configurations.

I claim:

1. A cardiac therapy system controlled by activity signals of the autonomous nervous system in a patient's body which constitute a measure for the patient's cardiovascular output requirement, for use with a conventional cardiac pacemaker circuit, the system comprising:
   pickup means for detecting at least the autonomous nervous system activity signals in the patient's body;
   control means for generating control signals as a function of time and/or intensity of the autonomous nervous system signals picked up in the patient's body by the pickup means;
   neurostimulator means for changing vascular resistance by nerve stimulation of the patient in adaptation to the patient's intracardial output requirement, in response to control signals from the control means;
   arrythmia suppressor means for generating antiarrhythmia stimulation pulses to the patient's heart which are controlled by control signals from the control means;
   and
   pump assist means for assisting the pumping of the patient's heart in response to control signals from the control means.

2. A therapy system according to claim 1, wherein the pickup means detects further signals in the patient's body which constitute a measure of external physical stress on the patient or the stress on body organs and wherein the control means generates the control signals in response to the detected further signals.

3. A therapy system according to claim 2, wherein the control means generates the control signals as a function of event patterns that are predetermined wherein the event patterns comprises:
   the occurrence of the autonomous nervous system signals within predetermined time windows,
   the frequency and/or intensity of the autonomous nervous system signals,
   the frequency and/or intensity of the further signals, external programming signals, and
   previously generated control signals generated earlier in this way.

4. A cardiac therapy system according to claim 1, wherein the activity signals of the autonomous nervous system include a regionally operative increase in the intracardial impedance in the region of the right ventricle of the patient's heart.

5. A cardiac therapy system according to claim 4, wherein the control means includes determination means for determining values of the activity signals of the autonomous nervous system in a range of maximum changes that are a function of the patient's activity.

6. A cardiac therapy system according to claim 1, wherein the autonomous nervous system activity is influenced by nociceptive stimuli and by the nerve stimulation by the neurostimulator means and/or the antiarrhythmia signals from the arrythmia suppressor means.

7. A cardiac therapy system for a patient having a heart, comprising:
   pickup means for detecting signals representative of the patient's cardiovascular function, the signals detected including at least autonomous nervous system signals;
   arrythmia suppressor means for producing antiarrythmia signals;
   pump assist means for assisting the pumping activity of the patient's heart;
   neurostimulator means for producing nerve stimulation signals; and
   control means for receiving the signals representative of the patient's cardiovascular function from the pickup means, and for generating control signals for controlling the arrythmia suppressor means, the pump assist means, and the neurostimulator means.

8. A cardiac therapy system according to claim 7, further comprising a pacemaker, wherein the control means further produces pacemaker control signals.

9. A cardiac therapy system according to claim 7, wherein the pickup means comprises:
   an intracardial impedance determining circuit, connected to a circuit for determining a regionally operative increase of the intracardial impedance in the region of the patient's heart's right ventricle, which is in turn connected to an activity value determining circuit, for producing the autonomous nervous system signals, wherein the autonomous nervous system signals represent information of activity values of the autonomous nervous system relating to intensity and time position during a cardiac time interval;
   and wherein the control means comprises:
   logic means for receiving and logically linking the autonomous nervous system signals from the pickup means, and memory means for generating the control signals for controlling the arrythmia suppressor means, the pump assist means, and the neurostimulator means.

10. A cardiac therapy system according to claim 9, wherein the pickup means further comprises pickups for detecting signals within the patient's body which are a measure of external physical stress, including stress on individual organs of the patient which are dependent on the external physical stress, and for outputting stress signals to the control means.

11. A cardiac therapy system according to claim 9, wherein the logic means comprises programmable means for receiving external programming signals which influence the operation of the logic means.

12. A cardiac therapy system according to claim 9, wherein the memory means receives as address input previously generated control signals.

13. A cardiac therapy system according to claim 7, wherein nerve stimulation signals from the neurostimulator means are applied to the patient for changing vascular resistance of the patient by nerve stimulation of the patient in adaptation to the patient's intracardial output requirement.

14. A cardiac therapy system controlled by activity signals of the autonomous nervous system in a patient's body which constitute a measure for the patient's cardiovascular output requirement, the system comprising:

pickup means for detecting at least the autonomous nervous system activity signals in the patient's body; and control means for generating control signals as a function of time and/or intensity of the autonomous nervous system signals picked up in the patient's body by the pickup means;

wherein the system further comprises at least one of:

neurostimulator means for changing vascular resistance by nerve stimulation of the patient in adaptation to the patient's intracardial output requirement, in response to control signals from the control means;

arrythmia suppressor means for generating anti-arrhythmia stimulation pulses to the patient's heart which are controlled by control signals from the control means; and pump assist means for assisting the pumping of the patient's heart in response to control signals from the control means.

* * * * *